United States Patent
Jarowski

(10) Patent No.: US 7,304,044 B2
(45) Date of Patent: Dec. 4, 2007

(54) LOWERING BLOOD GLUCOSE, UREA, CHOLESTEROL, TRIGLYCERIDES AND NORMALIZING HOMOCYSTEINE LEVELS BY DIETARY ADDITION OF SELECTED ESSENTIAL AMINO ACIDS AND THREE VITAMINS

(76) Inventor: Charles I. Jarowski, 67 Harbor La., Massapequa Park, NY (US) 11762

( * ) Notice: Subject to any disclaimer, the term of this patent is extended or adjusted under 35 U.S.C. 154(b) by 0 days.

(21) Appl. No.: 11/041,180

(22) Filed: Jan. 11, 2005

(65) Prior Publication Data

US 2006/0153910 A1    Jul. 13, 2006

(51) Int. Cl.
- A61K 31/70    (2006.01)
- A61K 31/495   (2006.01)
- A61K 31/44    (2006.01)
- A61K 31/40    (2006.01)
- A61K 31/195   (2006.01)

(52) U.S. Cl. .................... 514/52; 514/249; 514/345; 514/419; 514/561; 514/562

(58) Field of Classification Search ............... None
See application file for complete search history.

(56) References Cited

U.S. PATENT DOCUMENTS

| 3,080,234 A * | 3/1963 | Jarowski | 514/419 |
| 5,559,142 A * | 9/1996 | Jarowski | 514/419 |
| 6,602,909 B1 * | 8/2003 | Jarowski | 514/561 |
| 2004/0234631 A1* | 11/2004 | Hoie | 424/757 |

* cited by examiner

*Primary Examiner*—Raymond J. Henley, III

(57) ABSTRACT

Administration of a dietary supplement consisting of L-Tryptophan (80 mgs), L-Methionine (90 mgs), L-Valine (103 mgs), L-Lysine Monohydrochloride (128 mgs), Vitamin B-12 (0.5 mg), Vitamin B-6 (10 mgs), and Folic Acid (0.4 mg) has been shown to reduce postprandial peak blood glucose, lower urea formation, reduce cholesterol and triglyceride blood levels and normalize homocysteine blood levels.

The four amino acids are calculated to be limiting on the basis of the average fasting plasma profile of the essential amino acids when compared with the amino acid composition of 60 commonly consumed proteins. Depending upon the quantity of protein being consumed, one or two of the encapsulated supplement are required to effectively improve the quality of the protein.

1 Claim, No Drawings

LOWERING BLOOD GLUCOSE, UREA, CHOLESTEROL, TRIGLYCERIDES AND NORMALIZING HOMOCYSTEINE LEVELS BY DIETARY ADDITION OF SELECTED ESSENTIAL AMINO ACIDS AND THREE VITAMINS

INTRODUCTION

In his U.S. Pat. No. 6,602,909 the author claimed that supplementation of dietary proteins with L-Tryptophan (80 mgs.), L-Methionine (90 mgs.) L-Valine (103 mgs.) and L-Lysine Monohydrochloride (128 mgs.) would lower peak postprandial blood glucose levels and reduce urea formation. Studies conducted in a human volunteer consuming double and triple the recommended dose before each meal revealed that elevations in homocysteine blood levels occurred. Such undesirable elevations were avoided by the addition of the vitamins, B-12 (0.5 mg), B-6 (10 mgs.) and Folic Acid (0.4 mg.). The efficacy of the three vitamins had been reported to control homocysteine levels (1,2,3).

The addition of the three vitamins to the patented quartette of essential amino acids yields an improved dietary supplement with the additional claim that control of homocysteine levels as well as lowered peak blood glucose and lowered urea formation results.

Diets free of carbohydrate show very little rise in postprandial blood glucose, however the urinary urea level after such meals can be significantly reduced if the above dietary supplement is taken immediately before.

Consuming customary meals without supplementation for 30 days led to a level of 182 mgs % of Cholesterol and 220 mgs % of Triglyceride. Initiation of supplementation reduced the fasting blood level of Cholesterol to 168 mgs % and a triglyceride level of 118 mgs % in a pilot clinical study.

Use of the average fasting blood profile of the essential amino acids to determine their levels of supplementation has been described in earlier Patents (4,5,6).

EXPERIMENTAL

TABLE I

Postprandial Peak Blood Glucose and Urinary Urea Levels.

Protocol: Identical meals were consumed with and without supplementation. The encapsulated supplement consisted of L-Tryptophan (80 mgs.), L-Methionine (90 mgs.), L-Valine (103 mgs.), L-Lysine Hydrochloride (128 mgs.), Vitamin B-12 (0.5 mg), Vitamin B-6 (10 mgs.) and Folic Acid (0.4 mg). Urine samples were collected and pooled over a four hour period. Aliquots were frozen until assays were performed. A glucometer was used to measure blood glucose levels at several intervals of time. The urinary urea levels were measured colorimetrically.
BREAKFAST: Instant Rice (¼ Cup, Protein 3 grams, Carbohydrate 38 grams), Egg Albumin (3 tablespoonsfull, Protein 5 grams), Cow's Milk (1 Cup, Fat 1%, Protein 8 grams, Carbohydrate 12 grams), Multivitamin/Multimineral Capsule, Vitamin C Tablet (500 mgs) and Coffee (1 cup). Total Protein 16 grams.
The rice, Egg Albumin, Milk mixture was microwaved 3.5 minutes. The Fasting Blood Glucose measured 95 mgs %. Postprandial Values: 3 minutes: 93 mgs %; 13 minutes: 144 mgs %; 23 minutes: 208 mgs %; 53 minutes: 144 mgs %; 123 minutes: 102 mgs %. Urinary Urea (4 hour pooled sample): 2.27 grams.
Addition of 1 capsule containing the dietary supplement give the following postprandial blood glucose readings: 1 minute: 75 mgs %; 16 minutes: 112 mgs %; 41 minutes: 164 mgs %; 101 minutes: 147 mgs %; 146 minutes: 104 mgs %. Urinary Urea (4 hour pooled sample): 1.95 grams.

TABLE I-continued

Postprandial Peak Blood Glucose and Urinary Urea Levels.

URINARY UREA RECOVERY (24-HOUR)

PROTOCOL: Breakfast was consumed between 7:30 A.M. to 8:00 A.M. Lunch was eaten between 12 Noon and 12:30 P.M. Dinner was consumed between 6:00 P.M. and 6:30 P.M. Pooled urine was collected for 24 hours and an aliquot was frozen until the urea assays were conducted. Control meals were consumed on Monday. Supplemented meals were taken on Thursdays. Examples of typical meals used are presented.
Breakfast: Instant Rice (½ Cup, 6 grams of Protein, 76 grams of Carbohydrate), 1 Egg (12.8 grams of Protein), Cow's Milk (½ Cup, 1% Fat, Protein 4 grams Carbohydrate 6 grams) Evaporated Milk (10 ml, 0.7 gm of Protein, Carbohydrate 0.94 gm), 1 glass of Orange Juice, 1 teaspoonfull of Psyllium, 10 Ritz Crackers (10 gms of Protein, 100 grams of Carbohydrate), 1 Multivitamin/Multimineral tablet. Total Protein: 33.5 grams.
Lunch: 3 slices of Turkey Breast (3 grams of Protein), 2 Pieces of Potato Bread (8 grams of Protein, 30 grams of Carbohydrate), Swiss Cheese (5 grams of Protein), 1 Cup of Coffee, Evaporated Milk (10 ml, 0.7 gram of Protein, 0.94 gram of Carbohydrate). Total Protein: 16.7 grams.
Dinner: Swanson's Hungry Man Turkey Dinner (30 grams of Protein, 66 grams of Carbohydrate), 8 Ritz Crackers (8 gms of Protein, 80 gms Carb.), Coffee, 10 ml Evaporated Milk (Protein 0.7 gm, Carbohydrate 0.94 gm). Total Protein: 38.7 gms.
Urinary Urea (24-Hour Pooled Sample):

Without Supplement: 11.56 grams.
With 2 capsules of dietary supplement after each meal: 8.34 grams.

TABLE II

Homocysteine Blood Levels Following Administration of the Four Essential Amino Acids with and without Vitamins B12, B6 and Folic Acid.

Protocol: Hard gelatin #0 Capsules were filled with blends of L-Tryptophan (80 mgs), L-Methionine (90 mgs), L-Valine (103 mgs) and L-Lysine Monohydrochloride (128 mgs) with and without Vitamin B12 (0.5 mg), Vitamin B6 (10 mgs) and Folic Acid (0.4 mg). At monthly intervals the fasting blood levels of Homocysteine were determined.
1. One vitamin free capsule was taken before each meal.
   Fasting Homocysteine Blood Level: 15.6 micromoles per Liter.
2. Two vitamin free capsules were taken before each meal.
   Fasting Homocysteine Blood Level: 47.9 micromoles per Liter.
3. Three vitamin free capsules were taken before each meal.
   Fasting Homocysteine Blood Level: 61.5 micromoles per Liter.
4. Two capsules containing the four amino acids and three vitamins were taken before each meal
   Fasting Homocysteine Blood Level: 13 micromoles per Liter.

REFERENCES (1) D. L. McKay, G. Perrone, H. Rasmussen, G. Dallai and J. M. Blumberg, J. Nutr. 130, 3090-3099 (2000).

(2) M. C. McKinley, H. McNulty, J. McPartlin, L. Strain, K. Pentieva, M. Ward, D. G. Weir, and J. M. Scott, Am. J. Clin. Nutr., 73, 759-764 (2001).

(3) P. F. Jacques, J. Delhub, A. G. Bostum, P. W. F. Wilson, and I. H. Rosenberg, N. Engl. J. Med. 340, 1449-1454 (1999).

(4) U.S. Pat. No. 6,602,909 issued to C. I. Jarowski (Aug. 5, 2003).

(5) U.S. Pat. No. 5,559,142 issued to C. I. Jarowski (Sep. 24, 1996).

(6) U.S. Pat. No. 3,080,234 issued to C. I. Jarowski (Mar. 5, 1963).

What is claimed is:

1. A method for lowering postprandial blood glucose levels, lowering urinary urea levels, lowering blood cholesterol levels, lowering blood triglyceride levels and lowering blood homocysteine levels which comprises administering to a human in need thereof a dietary supplement comprising an encapsulated blend of 0.4 milligram of Folic Acid, 0.5 milligram of Vitamin B-12, 10 milligrams of Vitamin B-6, 80 milligrams of L-Tryptophan, 90 milligrams of L-Methionine, 103 milligrams of L-Valine and 128 milligrams of L-Lysine Hydrochloride.

* * * * *